(12) United States Patent
Goldfarb et al.

(10) Patent No.: US 6,290,645 B1
(45) Date of Patent: Sep. 18, 2001

(54) ENDOSCOPIC VIDEO CAMERA LAMP AND COUPLING ASSEMBLY

(75) Inventors: Michael A. Goldfarb; Eric Alan Goldfarb, both of Little Silver, NJ (US)

(73) Assignee: Dynamic Surgical Inventions LLC, Little Siver, NJ (US)

( * ) Notice: Subject to any disclaimer, the term of this patent is extended or adjusted under 35 U.S.C. 154(b) by 0 days.

(21) Appl. No.: 09/290,308

(22) Filed: Apr. 12, 1999

Related U.S. Application Data
(60) Provisional application No. 60/112,487, filed on Dec. 16, 1998.

(51) Int. Cl.[7] ....................................................... A61B 1/06
(52) U.S. Cl. ............................................ 600/249; 362/804
(58) Field of Search ................................. 600/122, 133, 600/249; 362/804, 399, 400, 457; 348/61, 66, 77, 143, 370, 373, 722; 396/12, 14, 199, 200, 419

(56) References Cited

U.S. PATENT DOCUMENTS

| | | | |
|---|---|---|---|
| 3,360,640 | 12/1967 | Seitz et al. ............................. | 240/1.4 |
| 3,891,842 | 6/1975 | Strusinski .............................. | 240/1.4 |
| 3,941,933 | 3/1976 | Shields .................................. | 179/1 H |
| 4,756,304 | 7/1988 | Watanabe . | |
| 4,831,456 | 5/1989 | Takamura .............................. | 358/229 |
| 4,878,485 | 11/1989 | Adair . | |
| 4,976,299 | 12/1990 | Bickelman ............................ | 150/155 |
| 5,010,876 | 4/1991 | Henley et al. ......................... | 128/6 |
| 5,153,783 | 10/1992 | Tamada et al. ..................... | 360/35.1 |
| 5,185,667 | 2/1993 | Zimmerman ........................ | 358/209 |
| 5,305,978 | 4/1994 | Current ................................ | 248/230 |
| 5,313,306 | 5/1994 | Kuban et al. .......................... | 348/65 |
| 5,347,431 | 9/1994 | Blackwell et al. .................... | 362/11 |
| 5,353,786 | 10/1994 | Wilk ...................................... | 128/23 |
| 5,498,230 | 3/1996 | Adair .................................... | 600/112 |
| 5,587,736 | 12/1996 | Walls .................................... | 348/65 |
| 5,716,323 | 2/1998 | Lee ....................................... | 600/134 |
| 5,803,905 | 9/1998 | Allred et al. .......................... | 600/249 |
| 5,868,664 | 2/1999 | Speier et al. ......................... | 600/112 |
| 5,884,996 | * 3/1999 | Cottone et al. ...................... | 362/399 |

FOREIGN PATENT DOCUMENTS 296 21 838
U1 * 4/1997 (DE) .

* cited by examiner

*Primary Examiner*—John Mulcahy
(74) *Attorney, Agent, or Firm*—Duane, Morris & Heckscher LLP

(57) ABSTRACT

A system is provided for photographing an open surgical procedure, comprising a high resolution endoscopic video camera, a surgical lamp having a handle covered by a sterile, compressible sheath and being positioned in spaced relation to the open surgical site, and a clamp for securing the video camera to the handle. A preferred clamp for securing the video camera to the handle is also provided.

4 Claims, 5 Drawing Sheets

ENDOSCOPIC VIDEO CAMERA LAMP AND COUPLING ASSEMBLY

This application claims priority from copending provisional patent Application Serial No. 60/112,487, filed Dec. 16, 1998, entitled Camera with Light.

FIELD OF THE INVENTION

The present invention generally relates to photographically recording open surgical procedures with the aid of existing operating room equipment in a sterile fashion, and more particularly to photographic recording of open surgical procedures where the physician requires personal control of the photography.

BACKGROUND OF THE INVENTION

It is often desirable to record various aspects of a surgical procedure for review and/or study by other physicians, surgical assistants, medical students, patients, or by insurers during quality review. As a result, numerous prior art systems and methods have been developed which provide means for recording the images of a medical procedure for storage in the form of videotape or still photographs.

Prior art surgical camera assemblies comprising a camera disposed in connection with mounting systems which provide for positioning of the camera relative to the surgical site in order to allow for still photography or remote viewing are well known in the art. These prior art systems often use dedicated photographic equipment, see for example U.S. Pat. No. 3,360,640, issued to Seitz et al., and U.S. Pat. No. 3,891,842, issued to Strusinski.

In U.S. Pat. No. 5,803,905, issued to Allred et al., a surgical camera assembly and method are disclosed in which the camera is attached to a retaining assembly that has replaced a surgical lamp's handle. A sterile bag is used to cover the complete camera assembly, and provides a sterile surface for gripping by a surgeon when orienting the lamp in relation to the procedure. The camera lens is removably disposed in operable engagement with the retaining assembly, and comprises an elongated body and a variable focus and zoom capability for producing visual images of the medical procedure site.

In order to take advantage of Allred's system, relatively expensive equipment must be purchased by the Hospital or surgeon. Significantly, this equipment is dedicated to the task of photographing an open surgical procedure operation. It would appear that Allred et. al., require that either an existing surgical lamp be partially disassembled and retrofitted or, a completely new lamp be purchased that includes Allred's system. Either alternative will require additional expenditure of scarce financial resources by the Hospital or physician. Also, reuse of a retrofitted lamp for surgery that does not require photography would appear to require that the camera be replaced with the original lamp handle to accommodate manipulation of the lamp. In addition, Allred et. al., attempt to solve the problem of sterilization by covering their apparatus with a sterile bag that is formed from a disposable material to provide a sterile gripping surface. This solution hinders the physician's ability to quickly and accurately adjust the camera and lamp during a surgical procedure. Most significantly, Allred et al., fail to utilize any of the camera or lighting equipment already in place in a typical operating theater without alterations or modification.

SUMMARY OF THE INVENTION

The present invention provides a system for photographing a medical procedure, comprising a high resolution endoscopic video camera, normally not intended for this purpose, a surgical lamp having a handle and sterile cover and being positioned in spaced relation to the surgical site, and a clamp adapted for securing the high resolution endoscopic video camera to the handle of the surgical lamp. The clamp comprises a camera receptacle and a handle receptacle. In one preferred embodiment, the camera receptacle has a shape that corresponds to the peripheral shape of the video camera, and includes a pair of confronting legs and a base extending between the pair of legs, and a pair of compression feet projecting inwardly from an end portion of each of the legs in coplanar relation to the legs and the base. The handle receptacle includes a pair of opposed, inwardly curved cantilevered beams that project outwardly from an upper portion of the compression feet in coplanar relation to the camera receptacle. The pair of opposed cantilevered beams also include complementary sets of teeth that are arranged to interengage with one another so as to create a ratchet effect when closing the handle receptacle around the lamp handle which is often preferably covered by a resilient sterile sleeve.

BRIEF DESCRIPTION OF THE DRAWINGS

These features and advantages of the present invention will be more fully disclosed in, or rendered obvious by, the following detailed description of the preferred embodiments of the invention, which are to be considered together with the accompanying drawings wherein like numbers refer to like parts and further wherein.

DETAILED DESCRIPTION OF THE PREFERRED EMBODIMENTS

Figure 1:
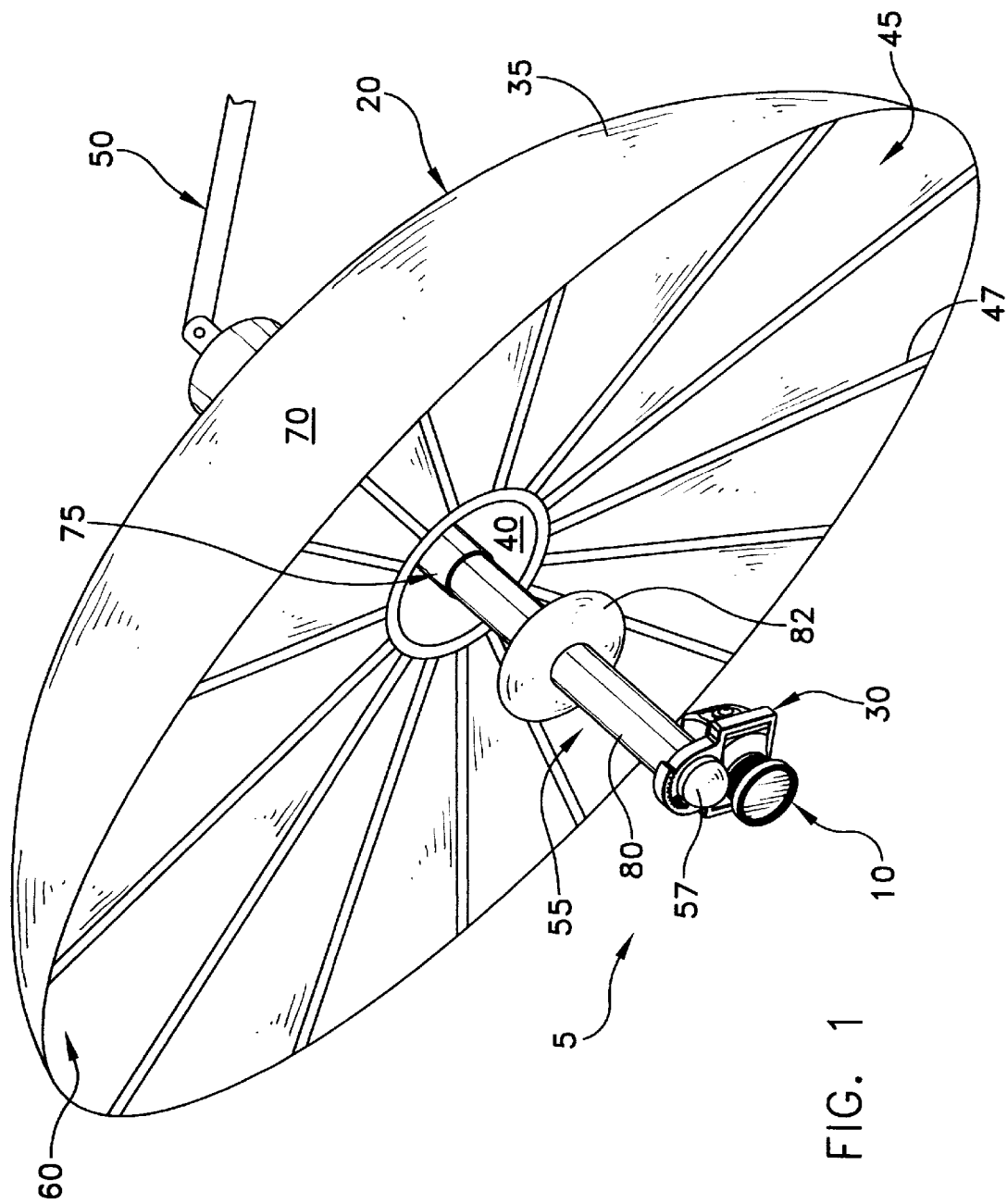
FIG. 1 is a perspective view of a high resolution endoscopic video camera, a surgical lamp, and a clamp according to one preferred embodiment of the present invention.
Figure 2:
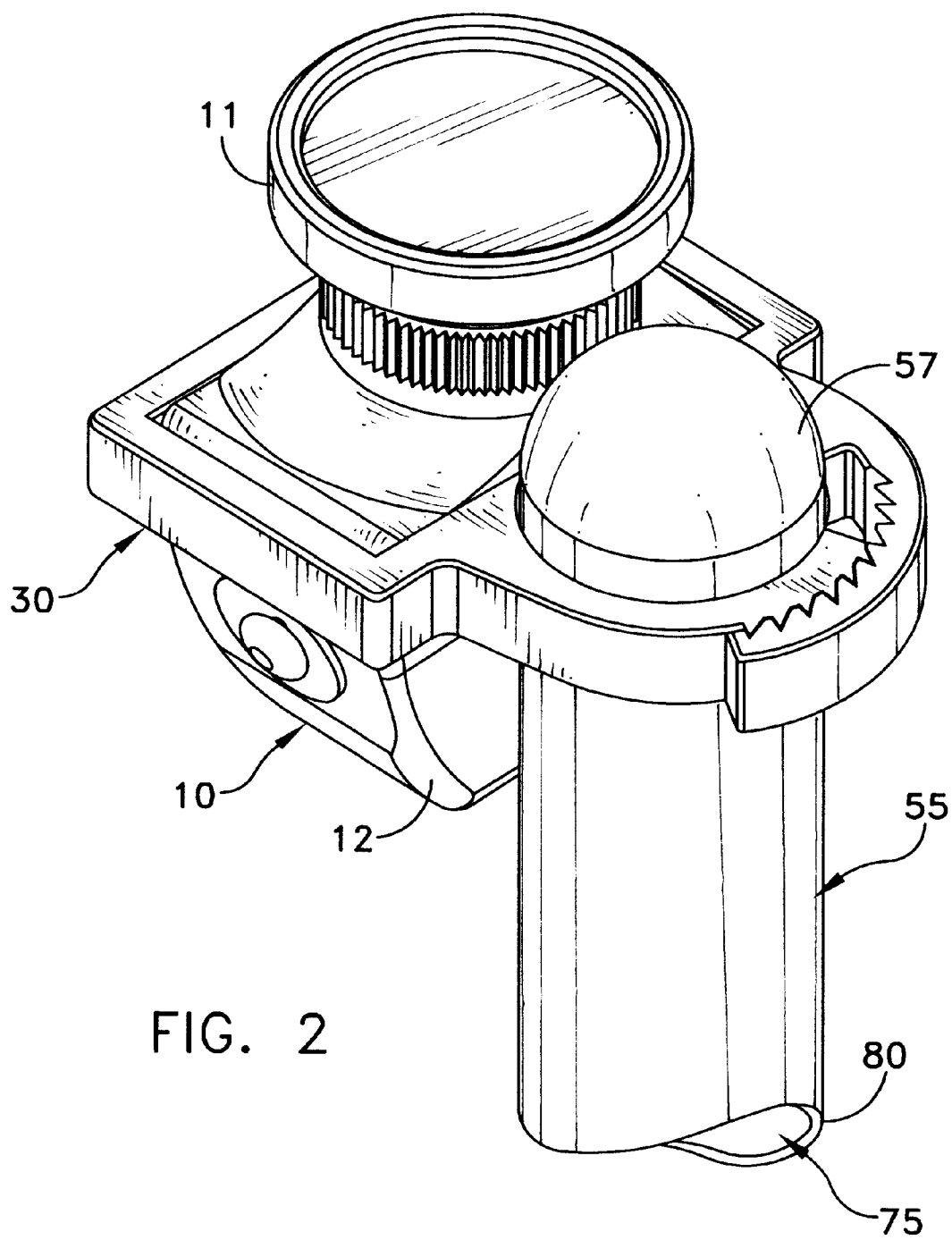
FIG. 2 is an enlarged perspective view of the video camera clamp and lamp handle shown in FIG. 1, with the lamp handle broken away from the remainder of the lamp for clarity of illustration.

FIG. 1 shows an endoscopic video camera and lamp assembly 5 that is adapted for photographing an open surgical procedure in accordance with a preferred embodiment of the present invention. Video camera and lamp arrangement 5 comprises a high resolution, endoscopic video camera 10, a lamp 20, and a clamp 30 (FIG. 2). High resolution it endoscopic video camera 10 generally comprises a lens 11, a body 12, and an electrical signal lead 13, and is of the type typically employed in endoscopic, general laparoscopic, or arthroscopic surgical procedures. U.S. Pat. No. 4,756,304, issued to Watanabe; 4,831,456, issued to Takamura; 4,878,485, issued to Adair; 5,001,736, issued to Kubota; 5,010,876, issued to Henley, et al.; 5,153,783, issued to Tamada et al.; 5,185,667, issued to Zimmermann; 5,313,306, issued to Kuban et al.; 5,587,736, issued to Walz; 5,716,323, issued to Lee; and 5,868,664, issued to Speier, et al., disclose a variety of high resolution video camera apparatus of the type broadly contemplated for use in connection with the present invention, which patents are hereby incorporated herein by reference.

High Resolution endoscopic video cameras of the type contemplated for use with the present invention often include three "CCD" chip technology and are capable of providing both live feed and still images. Parfocal zoom capabilities are also provided in these types of cameras, i.e., the lens system does not require refocusing after use of a zoom feature to enlarge the image. Typically, these types of parfocal zoom cameras have a variable focal length with a range of at least 25mm–50mm. Examples of high resolution video cameras that are particularly well suited for use with the present invention include the Endovision Tricam SL or DX, manufactured by Karl Storz, Inc., and the 882TE 3-chip standard camera system, manufactured by Stryker Endoscopy, Inc.

By way of further example only, the 882TE imaging system comprises a 1/3" interline transfer, hyper-HAD CCD, with 752 (horizontal)×582 (vertical) pixels. Its scanning system comprises 625 Lines, 2:1 interlaced 15,625 KHz (horizontal); 50Hz (vertical). Video outputs are provided including two NTSC standard 1.0V P—P into a 75 Ohm, BNC coaxial connector; two S-VHS components Y-1.0V, P—P C-0.29V, P—P 4-Pins S-VHS connector; and one RGB component 1.0 V P—P 75 ohm, 8 pin DIN connector. The 882TE endoscopic video camera contemplated for use with the present invention also comprises 900 horizontal TV lines, 450 vertical lines (frame integration) output capability. The signal-to-noise ratio is about 65 dB. Such endoscopic video cameras include mounting of their endoscope eyepiece using a coupler c-mount camera head, with c-mount scopes, e.g., (c-mount 1"-32 UN-2A). Such video cameras also require minimum illumination of about 1.1 Lux and have an auto shutter range of about 1/60 to 1/8,000 second. A gain of about 0 dB (off); +9 dB (on) is also typical of such high resolution video cameras. Their operating temperature may be in the range from about 50 to 104° F. (+10 to +40° C.), with a power consumption of about 30 watts, nominal. Input voltage range is often about 120+/−10 VAC 60/60 Hz. Normally, video cameras of the type used with the present invention have a weight of about 1 to 2 lbs or less.

Significantly, these high resolution, endoscopic video cameras have been expressly designed for inter connection with minimally invasive surgical procedures, such as endoscopic, laparoscopic and arthroscopic surgical procedures. These high resolution endoscopic video cameras would have normally not, heretofore, been considered by those skilled in the art for use in open surgical procedures, since their design and specifications have been developed exclusively for the physical and photographic requirements associated with minimally invasive surgical procedures and techniques.

Lamp 20 is of the type that is typically employed in conventional surgical theaters. More particularly, lamp 20 comprises a cowl 35, a bulb 40, a reflector/diffuser 45, a support 50, and a handle 55. Cowl 35 comprises a housing for structurally supporting the components of lamp 20. Often, cowl 35 is formed from a sheet of metal or the like so as to be bowl shaped, defining an interior recess and an exterior surface 70. Cowl 35 is structurally suitable for mounting other components of lamp 20, and may comprise various shapes and sizes without effect upon the novel aspects of the invention.

Bulb 40 comprises any of the well known light sources, such as incandescent lamps, fluorescent lamps, halogen lamps, etc. Reflector/diffuser 45 is shaped to be mounted within cowl 35, and is often curved so as to provide focus and direction to the light being emitted by bulb 40. Reflector/diffuser 45 may include surface features 47 designed to diffuse the light.

Lamp 20 includes support means 50 comprising either a floor stand or a ceiling or wall mount structure. These forms of support may include means for altering the position and direction of the light generated by bulb 40. Lamp 20 is useful with a wide variety of light supports, comprising various shapes and sizes, without effect upon the novel aspects of the invention.

Handle 55 is affixed to the center portion of cowl 35 so that lamp 20 may be adjusted by a surgeon to properly direct the light being emitted from bulb 40. Handle 55 comprises an elongate rod 75 that preferably projects outwardly from a central portion of lamp 20 (as shown in FIG. 1). Rod 75 is often formed from stainless steel or the like biocompatible material. Handle 55 includes a distal end 57 that is spaced away from the center of reflector/diffuser 45. Handle 55 is typically cylindrically shaped and sized for easy gripping by hand.

A resilient sleeve 80 is positioned over the surface of handle 55 so as to provide for firm gripping by the surgeon. Resilient sleeve 80 includes generally cylindrical, hollow body which is open at only one end and includes a guard 82 at the open end to prevent a surgeon's hand from sliding off the cover. The open end of the hollow body includes a retention member which is adapted to allow the handle to pass the retention member and slide into the interior of the hollow body. The retention member then acts to hold the cover in place over the handle during the surgical procedure. The retention member may comprise a cylindrical disc or the like which covers the open end of the hollow body and includes intersecting slits which form a cross-shaped opening. This opening is substantially less than the size of the open end of the hollow body but flexes to permit rod 75 to pass through.

Resilient sleeve 80 is particularly suitable for the cylindrical handle of an operating room lamp which must be touched by a surgeon. Resilient sleeve 80 is often formed from a sterilizable rubber or elastomeric polymer that is capable of storing energy when biased into a deformed state, i.e., when compressed. By way of example only, one resilient sleeve 80 that has provided excellent results when used in connection with the present invention is disclosed in U.S. Pat. No. 4,976,299, issued to Bickelman, which patent is hereby incorporated herein by reference.

Figure 3:
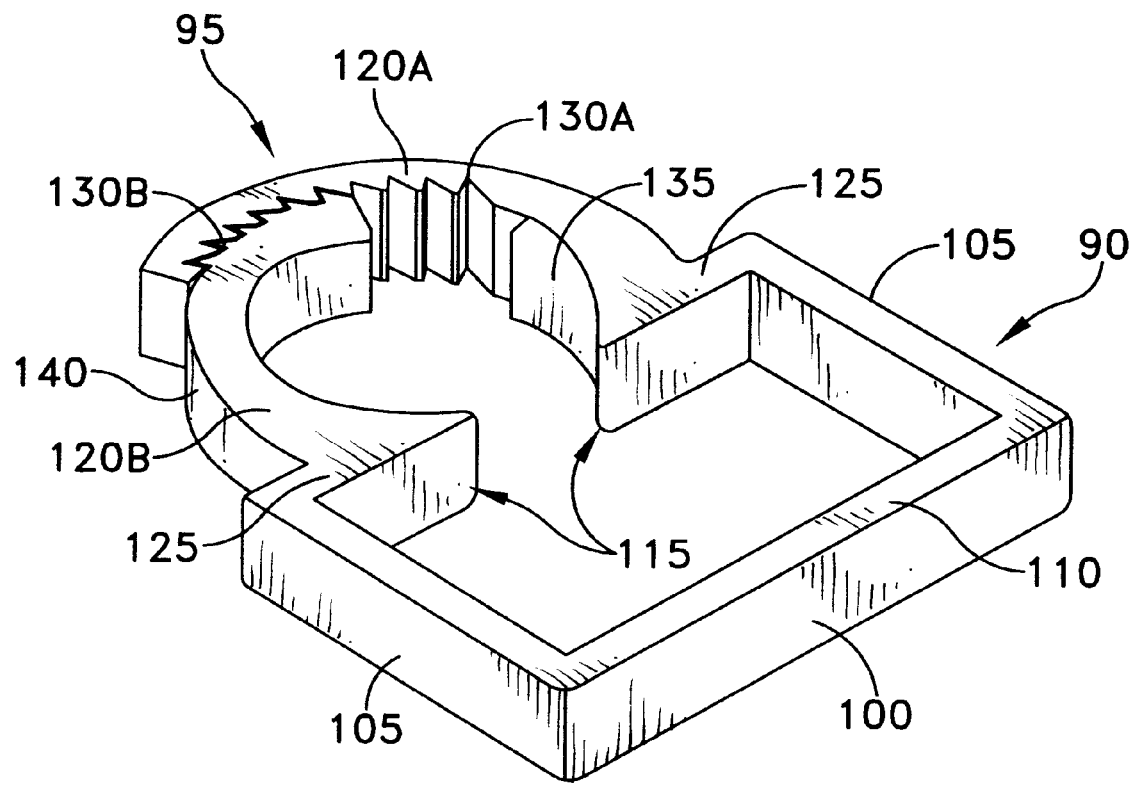
FIG. 3 is a perspective view of one preferred embodiment of a clamp.
Figure 4:
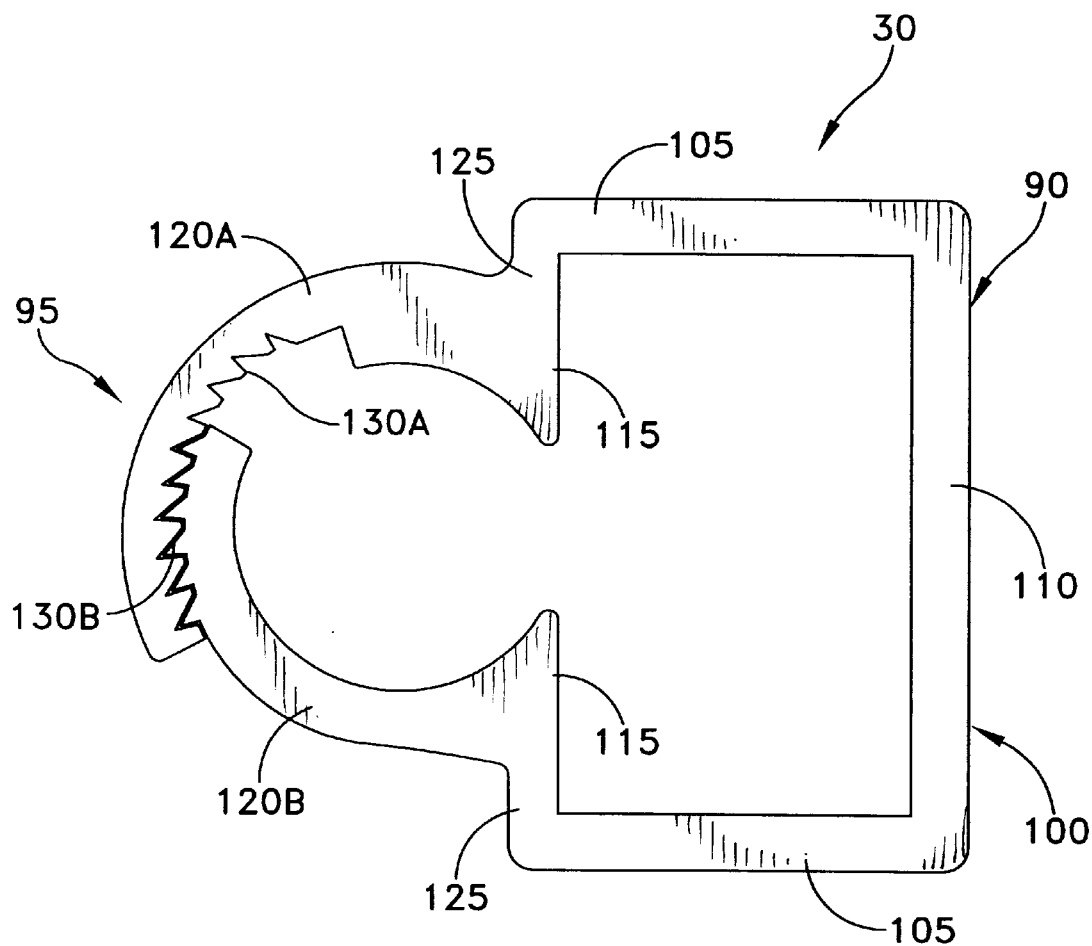
FIG. 4 is a front elevational view of the clamp shown in FIG. 3.

Referring in particular to FIGS. 3 and 4, clamp 30 is adapted to secure high resolution, endoscopic video camera 10 to handle 55, and comprises a camera receptacle 90 and a handle receptacle 95. Camera receptacle 90 defines a semiannular ring 100 having a shape that corresponds to the peripheral shape of any suitable high resolution, endoscopic video camera 10. When using an endoscopic video camera of the type mentioned hereinabove, semiannular ring 100 is generally shaped to fit the camera cross-sectional profile. Semiannular ring 100 is formed from a substantially resilient material, such as any one of the well known engineering polymers that have been found to be suitable for medical applications. Semiannular ring 100 may also be formed from a metal or composite material, as long as the selected material is sufficiently resilient, i.e., capable of storing energy when in a deformed state. Semiannular ring 100 includes a pair of confronting legs 105 and a base 110 that extends between legs 105. A pair of compression feet 115 project inwardly from end portions of legs 105, in coplanar relation to legs 105 and in coplanar, confronting relation to the inner surface of base 110.

Handle receptacle 95 is defined by a pair of opposed, inwardly curved cantilevered beams 120A, 120B that project outwardly from an upper portion 125 of each compression foot 115, and in coplanar relation to semiannular ring 100. First beam 120A includes a series of inwardly pointing teeth 130A on an inner surface 135. Second beam 120B includes a series of corresponding, outwardly pointing complementary teeth 130B on an outer surface 140. In the preferred embodiment, when first and second cantilevered beams 120A,120B are interengaged, a second, semiannular ring is formed having a shape that corresponds to the peripheral shape of handle 55. Of course, it will be understood that a variety of differently shaped handles may be accommodated by routine modifications to the shape and size of beams 120A, 120B, which modifications would comprise alternative handle receptacle means within the scope of the invention.

Pair of opposed cantilevered beams 120A,120B are formed from the same substantially resilient material as semiannular ring 100, and may also be formed from a metal or composite material, as long as the selected material is resilient, i.e., capable of storing energy when in a deformed state.

Figure 5:
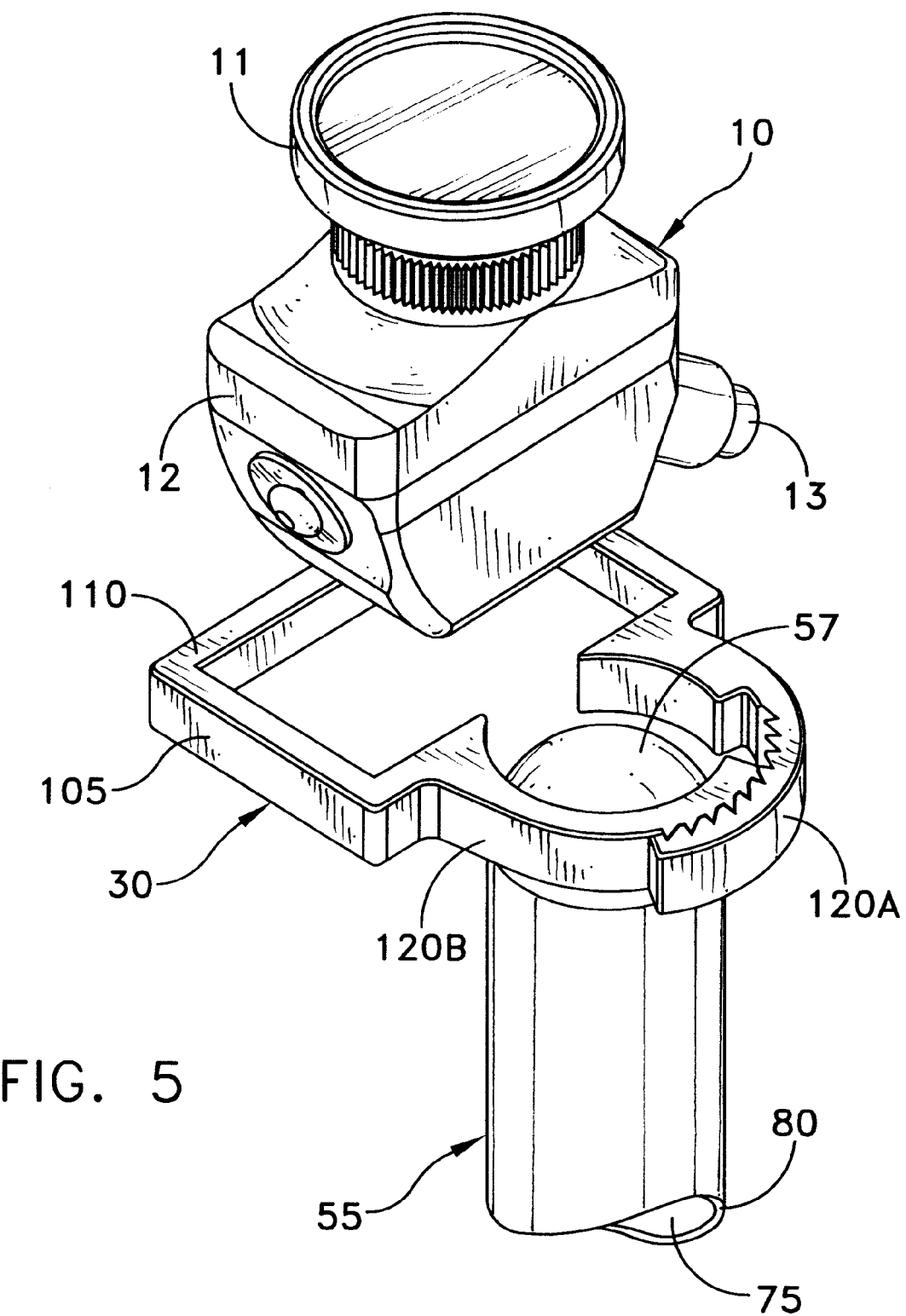
FIG. 5 is an exploded view of the video camera, lamp handle, and clamp shown in FIG. 2.

The system of the present invention is implemented in the following manner. Referring to FIG. 5, resilient sleeve 80 is first positioned overtop of handle 55, then clamp 30 is assembled to camera 10. More particularly, camera 10 is oriented so that body 12 is disposed in coaxial confronting relation with camera receptacle 90. Camera 10 is then moved toward clamp 30 until camera body 12 is disposed between legs 105 and base 110 of semiannular ring 100. Once in this position, camera 10 and clamp 30 may be assembled to handle 55 of lamp 20. Camera 10 and clamp 30 are positioned adjacent to distal end 57 of handle 55. In this position, distal end 57 is disposed in adjacent coaxial confronting relation to handle receptacle 95. It should be noted that curved cantilevered beams 120A, 120B may be interengaged at this point such that handle receptacle 95 defines an opening between cantilevered beams 120A and 120B that is somewhat larger than the diameter of handle 55 and resilient sleeve 80. Camera 10 and handle 30 are then moved toward handle 55 such that distal end 57 enters handle receptacle 95. Camera 10 and clamp 30 are then slid along handle 55 and resilient sleeve 80 to a position as is shown in FIG. 1.

Once in position, clamp 30 is squeezed so that teeth 130A, 130B of curved cantilever beams 120A,120B interdigitate or rachet, thus drawing handle receptacle 95 into tight engagement with resilient sleeve 80 and handle 55. As this occurs, compression feet 115 press against the side of body 12 of camera 10 thereby firmly retaining camera 10 within camera receptacle 90. It will be understood that as curved cantilever beams 120A and 120B rachet together, resilient sleeve 80 will compress and thereby store energy. At the same time, legs 105 and base 110 will bend inwardly, further engaging body 12 of camera 10, thus also storing energy. As a result, complementary teeth 130A, 130B will tend to be held in tight interengagement as a result of the storage of energy by resilient sleeve 80 and legs 105 and base 110.

In order to maneuver high resolution endoscopic video camera and lamp assembly 5 during surgery, a surgeon need only reach up and easily grasp any part of the assembly in normal fashion. Once surgery has been completed, high resolution endoscopic video camera and lamp assembly 5 may be disassembled by disengaging complementary teeth 130A, 130B. Once this occurs, clamp 30 is effectively released from its grip about handle 55 and camera 10. Clamp 30 can then be thrown away along with resilient sleeve 80, and camera 10 can be stored for future use.

Advantages Of The Invention

Numerous advantages are obtained by employing the present invention.

More specifically, a high resolution endoscopic video camera and lamp assembly is provided which avoids all of the aforementioned problems associated with prior art systems. These include the cost of dedicated photographic equipment, disassembly and adaptation of existing surgical lamps, difficulty in handling sterile bagged equipment, possible contamination by introduction of non-sterile conventional cameras or a photographer, and the expense of employing additional personnel to operate a remote controlled photographic system.

With the present invention, a high resolution endoscopic video camera and lamp assembly is provided that allows for either still or video records to be made for any open surgical procedure and allows for set up in several minutes by any member of the team using several readily available component parts.

Furthermore, a high resolution endoscopic video camera and lamp assembly is provided in which an existing high resolution endoscopic video camera and surgical lamp may be utilized to provide photographic records of open surgical procedures cost effectively and conveniently.

Also, a high resolution endoscopic video camera and lamp assembly is provided which is easily controlled by a surgeon during surgery so that the exact photographic record required by the surgeon can be obtained without additional effort.

Furthermore, a high resolution endoscopic video camera and lamp assembly is provided which allows all persons in the operating room, including personnel who normally have an obscured view, to follow the procedure.

Also, a high resolution endoscopic video camera and lamp assembly is provided with a sterile lamp handle cover and clamp that are disposable.

It is to be understood that the present invention is by no means limited to the precise constructions herein disclosed and shown in the drawings, but also comprises any modifications or equivalents within the scope of the claims.

What is claimed is:

1. A system for photographing medical procedures comprising:

a high resolution endoscopic video camera;

a surgical lamp having a handle including a resilient sleeve and being positioned in spaced relation to an active medical procedure site; and a clamp for securing said video camera to said handle, said clamp comprising a camera receptacle having a shape that corresponds to the peripheral shape of said video camera, including a semiannular ring comprising a pair of confronting legs and a base portion extending between said pair of legs and a pair of compression feet projecting inwardly from an end portion of each of said legs in coplanar relation to said legs and said base portion and a handle receptacle including a pair of opposed, inwardly curved cantilevered beams that project outwardly from an upper portion of said compression feet in coplanar relation to said semiannular ring of said camera receptacle.

2. A clamp for securing a high resolution endoscopic video camera to the handle of a surgical lamp, said clamp comprising:

a camera receptacle having a shape that corresponds to the peripheral shape of said video camera, including a semiannular ring comprising a pair of confronting legs and a base portion extending between said pair of legs and a pair of compression feet projecting inwardly from an end portion of each of said legs in coplanar relation to said legs and said base portion; and a handle receptacle including a pair of opposed, inwardly curved cantilevered beams that project outwardly from an upper portion of said compression feet in coplanar relation to said semiannular ring of said camera receptacle.

3. A system for photographing an open surgical site comprising:

a high resolution endoscopic video camera;

a lamp having a handle and being positioned in spaced relation to said surgical site;

a resilient sleeve disposed on at least a portion of said handle; and a clamp comprising a camera receptacle having a shape that corresponds to the peripheral shape of said video camera and a handle receptacle including means for securely and releasably engaging said handle so as to compress said resilient sleeve.

4. A system according to claim 3 wherein said resilient sleeve includes a generally cylindrical, hollow body which is open at only one end and includes a guard at said open end.

* * * * *